(12) United States Patent
Kheradvar et al.

(10) Patent No.: US 7,331,991 B2
(45) Date of Patent: Feb. 19, 2008

(54) IMPLANTABLE SMALL PERCUTANEOUS VALVE AND METHODS OF DELIVERY

(75) Inventors: Arash Kheradvar, Pasadena, CA (US); Guruswami Ravichandran, Arcadia, CA (US); Morteza Gharib, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 150 days.

(21) Appl. No.: 11/361,850

(22) Filed: Feb. 24, 2006

(65) Prior Publication Data

US 2006/0195180 A1 Aug. 31, 2006

Related U.S. Application Data

(60) Provisional application No. 60/756,705, filed on Jan. 6, 2006, provisional application No. 60/748,345, filed on Dec. 6, 2005, provisional application No. 60/657,474, filed on Mar. 1, 2005, provisional application No. 60/656,466, filed on Feb. 25, 2005.

(51) Int. Cl.
A61F 2/06 (2006.01)

(52) U.S. Cl. ............ 623/1.22; 623/1.26; 623/1.3; 623/900; 623/910; 623/904

(58) Field of Classification Search ......... 623/1.11, 623/1.22, 2.33, 2.1, 2.12, 2.11, 2.13, 2.14, 623/2.24, 2.38, 1.23, 1.24, 1.26, 1.3, 1.15, 623/1.18, 1.19, 900, 901, 902, 903, 909, 623/915; 128/203.11; 427/2.24

See application file for complete search history.

(56) References Cited

U.S. PATENT DOCUMENTS

| | | |
|---|---|---|
| 4,451,936 A | 6/1984 | Carpentier et al. |
| 4,692,164 A | 9/1987 | Dzemeshkevich et al. |
| 4,759,758 A | 7/1988 | Gabbay |
| 4,790,843 A | 12/1988 | Carpentier et al. |
| 4,851,001 A | 7/1989 | Taheri |
| 4,994,077 A | 2/1991 | Dobben |
| 5,032,128 A | 7/1991 | Alonso |
| 5,037,434 A | 8/1991 | Lane |
| 5,080,668 A | 1/1992 | Bolz et al. |
| 5,163,953 A | 11/1992 | Vince |
| 5,282,847 A | 2/1994 | Trescony et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,552 A | 5/1995 | Andersen et al. |
| 5,445,626 A | 8/1995 | Gigante |
| 5,500,014 A | 3/1996 | Quijano et al. |
| 5,545,214 A | 8/1996 | Stevens |
| 5,571,175 A | 11/1996 | Vanney et al. |
| 5,591,195 A | 1/1997 | Taheri et al. |
| 5,607,464 A | 3/1997 | Trescony et al. |
| 5,609,626 A | 3/1997 | Quijano et al. |
| 5,749,890 A | 5/1998 | Shaknovich |
| 5,824,064 A | 10/1998 | Taheri |
| 5,840,081 A | 11/1998 | Andersen et al. |

(Continued)

*Primary Examiner*—Ehud Gartenberg
*Assistant Examiner*—Jonathan R Stroud
(74) *Attorney, Agent, or Firm*—Scott C Harris, Esq.

(57) ABSTRACT

An implantable prosthetic valve that is transformable from a first helical pre-implantation configuration to a second valvular functional configuration, and methods of delivery.

37 Claims, 13 Drawing Sheets

U.S. PATENT DOCUMENTS

| | | |
|---|---|---|
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,954,766 A | 9/1999 | Zadno-Azizi et al. |
| 5,957,949 A | 9/1999 | Leonhardt et al. |
| 6,077,298 A | 6/2000 | Tu et al. |
| 6,106,550 A | 8/2000 | Magovern et al. |
| 6,106,551 A | 8/2000 | Crossett et al. |
| 6,132,473 A | 10/2000 | Williams et al. |
| 6,168,614 B1 | 1/2001 | Andersen et al. |
| 6,206,911 B1 | 3/2001 | Milo |
| 6,283,127 B1 | 9/2001 | Sterman et al. |
| 6,454,799 B1 | 9/2002 | Schreck |
| 6,458,153 B1 | 10/2002 | Bailey et al. |
| 6,482,228 B1 | 11/2002 | Norred |
| 6,530,952 B2 | 3/2003 | Vesely |
| 6,569,196 B1 | 5/2003 | Vesely |
| 6,582,462 B1 | 6/2003 | Andersen et al. |
| 6,638,239 B1 | 10/2003 | Bergheim et al. |
| 6,652,578 B2 | 11/2003 | Bailey et al. |
| 6,666,841 B2 | 12/2003 | Gharib et al. |
| 6,730,118 B2 | 5/2004 | Spenser et al. |
| 6,736,791 B1 | 5/2004 | Tu et al. |
| 6,780,164 B2 | 8/2004 | Bergheim et al. |
| 6,830,584 B1 | 12/2004 | Seguin |
| 6,830,585 B1 | 12/2004 | Artof et al. |
| 6,890,350 B1 | 5/2005 | Walak |
| 6,896,690 B1 | 5/2005 | Lambrecht et al. |
| 6,908,481 B2 | 6/2005 | Cribier |
| 6,945,957 B2 | 9/2005 | Freyman |
| 6,951,571 B1 | 10/2005 | Srivastava |
| 6,955,656 B2 | 10/2005 | Bergheim et al. |
| 6,974,476 B2 | 12/2005 | McGuckin, Jr. et al. |
| 7,007,698 B2 | 3/2006 | Thornton |
| 7,044,966 B2 | 5/2006 | Svanidze et al. |
| 7,081,131 B2 | 7/2006 | Thornton |
| 7,101,396 B2 | 9/2006 | Artof et al. |
| 2006/0025855 A1* | 2/2006 | Lashinski et al. ............ 623/2.1 |

* cited by examiner

IMPLANTABLE SMALL PERCUTANEOUS VALVE AND METHODS OF DELIVERY

CROSS-REFERENCE TO RELATED APPLICATIONS

This application claims priority of provisional application No. 60/656,466, filed Feb. 25, 2005, provisional application No. 60/657,474, filed Mar. 1, 2005, provisional application No. 60/748,345, filed Dec. 6, 2005, and provisional application No. 60/756,705, filed Jan. 6, 2006, all of which are incorporated in their entireties by reference herein.

FIELD OF THE INVENTION

The present invention is related to a prosthetic valve system for implantation in a body channel of a patient, more particularly, to an implantable prosthetic heart valve suitable for replacement of a defect or diseased human heart valve and methods of delivery.

BACKGROUND OF THE INVENTION

Human heart valves under the conditions of normal physiological functions are passive devices that open under the pressure of blood flow on their leaflets. Four valves in the heart serve to direct the flow of blood through all chambers in a forward direction. In addition to the four heart valves (tricuspid valve, mitral valve, aortic valve, and pulmonary valve), a patient has other flow-regulatory valves, such as venous valves, sphincter valves, and the like.

When disease conditions affect the structure or the materials of the native valve, the valve itself will decay, degenerate or disrupt and require repair or replacement to restore proper function necessary for the continuation of life.

U.S. Pat. No. 4,451,936 to Carpentier et al., entire contents of which are incorporated herein by reference, discloses an aortic prosthetic valve for supra-annular implantation comprising a valve body of generally annular configuration and a valve element movably mounted on the valve body for opening and closing the valve, and a scalloped suture ring circumscribing the valve body adjacent the base surface and configured to approximately fit the contour of the Sinuses of Valsalva at the base of the aorta.

U.S. Pat. No. 4,790,843 to Carpentier et al., entire contents of which are incorporated herein by reference, discloses a prosthetic heart valve assembly that includes an artificial annulus, a prosthetic valve and a retaining ring for releasably retaining the prosthetic valve on the artificial annulus. By removing the retaining ring, the valve can be replaced with another valve.

U.S. Pat. No. 4,994,077 to Gabbay, entire contents of which are incorporated herein by reference, discloses an improved prosthetic heart valve comprising a support body or stent covered by a layer of biological tissue having only the smooth surfaces thereof presented outwardly. The valve cusp is made of pericardial tissue that has been doubled over such that the rough side thereof is folded inwardly.

U.S. Pat. No. 4,994,077 to Dobben, entire contents of which are incorporated herein by reference, discloses a valve system consisting of a cylindrical or crown shaped stent that is made by bending wire into a zigzag shape to anchor the device and attach the flow regulator flap of a valve. The device presents significant hemodynamic, delivery, fatigue and stability disadvantages.

U.S. Pat. No. 5,163,953 to Vince, entire contents of which are incorporated herein by reference, discloses a valve system consisting of a flow-regulation mechanism of a flap of biologic material that is mounted inside a stent comprised of a toroidal body formed of a flexible coil of wire. The main shortcoming of this design is the profile and configuration, thus making the device clinically ineffective as a minimally invasive technique.

U.S. Pat. No. 5,332,402 to Teitelbaum, entire contents of which are incorporated herein by reference, discloses a valve system consisting of shape memory Nitinol and a flow-regulating valve. The stent-like support is comprised of a meshwork or braiding of Nitinol wire with trumpet-like distal and proximal flares. The flared ends are intended to maintain the position of the stent component across the valve thereby anchoring the device. The disadvantages of the device are the reduced valve orifice and sub-optimal hemodynamic characteristics.

U.S. Pat. No. 5,370,685 to Stevens, entire contents of which are incorporated herein by reference, discloses a percutaneous valve replacement system for the endovascular removal of a malfunctioning valve followed by replacement with a prosthetic valve. The valve replacement system may include a prosthetic valve device comprised of a stent and cusps for flow-regulation such as a fixed porcine aortic valve, a valve introducer, an intraluminal procedure device, a procedure device capsule and a tissue cutter. The valve device disclosed requires a large delivery catheter and intraluminal-securing means such as suturing to anchor the device at the desired location.

U.S. Pat. No. 5,397,351 to Pavcnik et al., entire contents of which are incorporated herein by reference, discloses a self-expanding percutaneous valve comprised of a poppet, a stent and a restraining element. The valve stent has barbed means to anchor to the internal passageway. The device includes a self-expanding stent of a zigzag configuration in conjunction with a cage mechanism comprised of a multiplicity of crisscrossed wires and a valve seat. The disadvantages of the device include large delivery profile, reduced effective valvular orifice, and possible perivalvular leakage.

U.S. Pat. No. 5,411,552 to Andersen et al., entire contents of which are incorporated herein by reference, discloses various balloon expandable percutaneous prosthetic valves. One embodiment discloses a valve prosthesis comprised of a stent made from an expandable cylindrical structure and an elastically collapsible valve mounted to the stent. The device is placed at the desired location by balloon expanding the stent and the valve. The main disadvantage to this design is the 20+ French size delivery catheters.

U.S. Pat. No. 5,445,626 to Gigante, entire contents of which are incorporated herein by reference, discloses a valve operated catheter for urinary incontinence and retention comprising a flexible duct designed to be inserted in the patient's urethra, the catheter provided with a spiral shaped end portion, having a plurality of holes for the passage of urine. The duct is provided, at its other end, with a seat in which there is housed a valve made of elastic material, the valve being usually closed because of the elastic action.

U.S. Pat. No. 5,500,014 to Quijano et al., entire contents of which are incorporated herein by reference, discloses a biological valvular prosthesis comprising a chemically fixed conduit derived from a harvested vein segment bearing at least one integrally formed venous valve, and a restriction means positioned about the conduit at either side of the venous for restricting the venous valve from expanding outwardly.

U.S. Pat. No. 5,824,064 to Taheri, entire contents of which are incorporated herein by reference, discloses an aortic valve replacement system combined with an aortic arch graft. The devices and percutaneous methods described require puncture of the chest cavity.

U.S. Pat. No. 5,855,597 to Jayaraman, entire contents of which are incorporated herein by reference, discloses a device comprising a star-shaped stent, a replacement valve and a replacement graft for use in repairing a damaged cardiac valve. The device is comprised of a chain of interconnected star-shaped stent segments in the center of which sits a replacement valve. The flow-regulation mechanism consists of three flaps cut into a flat piece of graft material that is rolled to form a conduit in which the three flaps may be folded inwardly in an overlapping manner.

U.S. Pat. No. 5,855,601 to Bessler et al., entire contents of which are incorporated herein by reference, discloses methods and devices for the endovascular removal of a defective heart valve and the replacement with a percutaneous cardiac valve. The device is comprised of a self-expanding stent member with a flexible valve disposed within. The stent member is of a self-expanding cylindrical shape made from a closed wire in a zigzag configuration that can be a single piece, stamped, extruded or formed by welding the free ends together. The flow-regulation mechanism is comprised of an arcuate portion that contains a slit to form leaflets and a cuff portion that is sutured to the stent and encloses the stent. The preferred flow regulator is a porcine pericardium with three cusps.

U.S. Pat. No. 5,925,063 to Khosravi, entire contents of which are incorporated herein by reference, discloses a percutaneous prosthetic valve comprised of a coiled sheet stent to which a plurality of flaps are mounted on the interior surface to form a flow-regulation mechanism that may be comprised of a biocompatible material. The disadvantages of this design include problematic interactions between the stent and flaps in the delivery state, and the lack of a detailed mechanism to ensure that the flaps will create a competent one-directional valve.

U.S. Pat. No. 5,954,766 to Zadano-Azizi et al., entire contents of which are incorporated herein by reference, discloses a device in which flow-regulation is provided by a flap disposed within a frame structure capable of taking an insertion state and an expanded state. The preferred embodiment of the flow-regulation mechanism is defined by a longitudinal valve body made of a sufficiently resilient material with a slit that extends longitudinally through the valve body.

U.S. Pat. No. 5,957,949 to Leonhardt et al., entire contents of which are incorporated herein by reference, discloses a prosthetic valve comprised of a tubular graft having radially compressible annular spring portions and a flow regulator, which is preferably a biological valve disposed within. In addition to oversizing the spring stent by 30%, anchoring means is provided by a light-activated biocompatible tissue adhesive that is located on the outside of the tubular graft and seals to the living tissue. Disadvantages of this device include those profile concerns, a large diameter complex delivery system, and feasibility of the light actuated anchoring means.

U.S. Pat. No. 6,106,550 to Magovern et al., entire contents of which are incorporated herein by reference, discloses an implantable apparatus for receiving a heart valve, comprising an annular ring having an inner wall and an outer wall, a plurality of channels displaced circumferentially about the ring, each channel extending from the inner wall to the outer wall, and a plurality of tissue attachment pins each pin being movable in a respective one of the channels between a first position during implantation, and a second position wherein the first end of each pin extends beyond the outer wall for tissue attachment.

U.S. Pat. No. 6,168,614 to Andersen et al., entire contents of which are incorporated herein by reference, discloses a method of endovascularly delivering a valve through a blood vessel, comprising the steps of providing a tissue valve and an expandable support structure, connecting the tissue valve to the support structure, and securing the tissue valve and the support structure to a desired valve location with the support structure in the expanded shape.

U.S. Pat. No. 6,206,911 to Milo, entire contents of which are incorporated herein by reference, discloses an expandable stent that is created so as to undergo essentially no axial foreshortening when expanded from an unexpanded or compressed configuration to an operative configuration. Attachment to the surrounding tissue may be via pairs of needle-like projections or prongs that may be bent to have a radial orientation during the deployment phase.

U.S. Pat. No. 6,283,127 to Sterman et al., entire contents of which are incorporated herein by reference, discloses a device system and methods facilitating intervention within the heart or a great vessel without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum.

U.S. Pat. No. 6,530,952 to Vesely, entire contents of which are incorporated herein by reference, discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing whereas a new collapsible valve is then installed, to resume the function of the prosthesis.

U.S. Pat. No. 6,582,462 to Andersen et al., entire contents of which are incorporated herein by reference, discloses a valve prosthesis for implantation in a body channel by way of catheterization, the prosthesis comprising a radially collapsible and expandable cylindrical stent and a collapsible and expandable valve having commissural points wherein the valve is mounted to the stent at the commissural points.

U.S. Pat. No. 6,569,196 to Vesely, entire contents of which are incorporated herein by reference, discloses a system for minimally invasive insertion of a bioprosthetic heart valve. The system includes a collapsible tissue-based valve system, a catheter-based valve delivery system, a surgical platform and a device tracking and visualization system, wherein the collapsible valve system includes a permanent outer frame that is affixed to the patient using conventional sutures or staples and a collapsible valve having a collapsible inner frame that mates with the outer frame.

U.S. Pat. No. 6,652,578 to Bailey et al., entire contents of which are incorporated herein by reference, discloses a catheter system with minimally invasive techniques for percutaneous and transluminal valvuloplasty and prosthetic valve implantation.

U.S. Pat. No. 6,830,584 to Seguin, entire contents of which are incorporated herein by reference, discloses a device for replacing, via a percutaneous route, a heart valve located in a bodily vessel, comprising an elongated support element, two series of elongated blades arranged around the circumference of the elongated elements, where the blades have opposite cutting edges and can be extended corolla-shaped such that their cutting edges are set in the extension of one another thereby forming circular cutting edges to cut the native valve so as to separate it from the corporeal duct.

U.S. Pat. No. 6,830,585 to Art of et al., entire contents of which are incorporated herein by reference, discloses a percutaneously deliverable heart valve with a plurality of valvular leaflets, the plurality of leaflets being sewn together at least a potion of their side edges to form an annulus at about the in-flow edge and a plurality of commissure tissues.

U.S. Pat. No. 6,896,690 to Lambrecht et al., entire contents of which are incorporated herein by reference, discloses a device for performing intravascular procedures wherein at least a portion of the device is configured for placement in a flowpath of a blood vessel. The device comprises a valve means configured to allow greater antegrade flow than retrograde flow through the vessel and a filter operative to restrict the passage of emboli while allowing blood flow through the vessel.

U.S. Pat. No. 6,908,481 to Cribier, entire contents of which are incorporated herein by reference, discloses a valve prosthesis comprising a collapsible, elastic valve member, an elastic stent member in which the valve member is mounted, and a support coupled to the valve member and positioned between the valve member and the stent member, wherein the stent member forms a continuous surface and comprises strut members that provide a structure sufficiently rigid to prevent eversion.

U.S. Pat. No. 6,951,571 to Srivastava, entire contents of which are incorporated herein by reference, discloses a valve-implanting device comprising a collapsible frame, inner and outer guide wires removably connected to the collapsible frame, and a plurality of valve flaps attached to the collapsible frame.

U.S. Pat. No. 6,974,476 to McGuckin, Jr. et al., entire contents of which are incorporated herein by reference, discloses a valve system comprising a first substantially annular portion adapted to be positioned on a proximal side of the annulus of a patient and a second substantially annular portion adapted to be positioned on a distal side of the annulus of a patient, wherein at least one of the first and second substantially annular portions is movable towards the other portion to a clamped position to clamp around the annulus. The second portion has a flow restricting apparatus.

Each of the prior art stent valve designs has certain disadvantages which are resolved by the present embodiments. The prior art valve prosthesis generally consists of a support structure with a tissue valve connected to it, wherein the support structure is delivered in a collapsed shape intraluminally and secured to a desired valve location with the support structure in the expanded shape. However, the support structure tends to compressively impinge a portion of the leaflets of the tissue valve at the structure struts when the support structure is expanded by an inflatable balloon for positioning endovascularly. The impinged leaflets tend to deteriorate and calcify, making the valve useless.

SUMMARY OF THE INVENTION

A valve system with minimal profile and no tissue impingement concerns during the delivery phase is disclosed in some embodiments. Some aspects of the invention relate to a prosthetic valve for implantation in a patient comprising a first helical pre-implantation configuration and a second valvular post-implantation configuration, wherein the first configuration is reversibly transformable to the second configuration. In one embodiment, the first pre-implantation configuration is characterized with a non-functional valve whereas the second post-implantation configuration is characterized with a functional operative valve.

One object of the invention provides a prosthetic valve that comprises a support structure with leaflets mounted thereon, wherein the leaflets are made from material selected from the group consisting of synthetic material, engineered biological tissue, biological valvular leaflet tissue, pericardial tissue, and crosslinked pericardial tissue. In one embodiment, the pericardial tissue is selected from the group consisting of bovine, equine, porcine, ovine, and human tissue. In one embodiment, the crosslinked pericardial tissue is crosslinked with a crosslinking agent selected from the group consisting of formaldehyde, glutaraldehyde, dialdehyde starch, glyceraldehydes, cyanamide, diimides, diisocyanates, dimethyl adipimidate, carbodiimide, epoxy compounds, and mixtures thereof.

One object of the invention provides a prosthetic valve that comprises a support structure with leaflets mounted thereon, the support structure comprising a circular or circular-like stent and a plurality of elongate support arms, wherein a first of the elongate support arm is splittable into two support beams along a longitudinal elongate axis of the first support arm. In one embodiment, the stent is splittable at about the base of the split beams. In a further embodiment, the stent or the support structure of the present invention is made of shape memory material, self-expanding Nitinol, or thermal shape memory Nitinol.

One object of the invention provides a prosthetic valve that comprises a support structure with a circular or circular-like stent and a plurality of elongate support arms, wherein a first support arm is splittable into two support beams, wherein the two support beams are coupled to each other by a magnetic force at the second valvular post-implantation configuration. In an alternate embodiment, a first of the two support beams is coupled to a second of the two support beams by a suture and cinch technique at the second valvular post-implantation configuration. In a further embodiment, at least a portion of the support structure is covered with cloths. In one embodiment, the prosthetic valve comprises at least a hook, a coil, a screw, or clasp-like mechanism at a distal end of the support arms adapted for locking the valve in the crown structure. In a further embodiment, the prosthetic valve comprises at least a hook, or hook-like anchoring mechanism at a distal end of the support arms adapted for stabilizing the valve at the implant site by piercing into the surrounding tissue.

One object of the invention provides a prosthetic valve that comprises a support structure with a circular or circular-like stent, wherein the stent is splittable into a non-circular stent with two ends, wherein the two ends are coupled to each other by a magnetic force or by a suture and cinch technique at the second valvular post-implantation configuration. In a further embodiment, at least a portion of the support structure is covered with cloths. In a further embodiment, the prosthetic valve comprises at least a hook or hook-like anchoring mechanism at a distal end of the support arms adapted for stabilizing the valve at the implant site.

One object of the invention provides a prosthetic valve that comprises a first helical configuration that converts to a second circular, semi-circular, or circular-like support structure with leaflets mounted there on. The support structure is covered by biocompatible clothing. The clothing can also be elongated or extended at some points, such as supporting arms or split support beams, that attaches to the leaflets. The cloths-covered arms would be locked inside the crown structure with at least a hook or hook-like anchoring mechanism at a proper place for stabilizing the valve at the implant site by piercing into the surrounding tissue.

Some aspects of the invention relate to a prosthetic valve system for implantation in a body channel comprising: a prosthetic valve having a first helical pre-implantation configuration that is reversibly transformable to a second valvular configuration; and a radially or helically collapsible and expandable crown, the crown including a cylindrical support means for enclosing or securing the prosthetic valve. In one embodiment, the prosthetic valve system further comprises an elongate delivery apparatus, wherein the prosthetic valve at the first pre-implantation configuration and the crown are collapsibly mounted onto the delivery apparatus.

One object of the invention provides a prosthetic valve system, wherein the crown is expandable by an inflatable balloon technique. In one embodiment, the crown of the prosthetic valve system is self-expandable or temperature-sensitive thermal expandable that is made of a shape memory material or of shape memory Nitinol. In one embodiment, the prosthetic valve is attached to the cylindrical support means of the crown.

One object of the invention provides a prosthetic valve system, wherein the prosthetic valve at the first pre-implantation configuration is removably mounted onto the delivery apparatus in a helically collapsed manner on the elongate delivery apparatus. In one embodiment, the profile of the mounted prosthetic valve is about 3 to 12 French diameters, preferably about 3 to 6 French diameters.

One object of the invention provides a prosthetic valve system, wherein an exterior surface of the delivery apparatus comprises a helical groove sized and configured to receive the mounted prosthetic valve at its helically collapsed manner. In one embodiment, the delivery apparatus is selected from the group consisting of a catheter, a wire, a guidewire, a flexible tubing, and a cannula. In one embodiment, the prosthetic valve comprises a support structure with a circular or circular-like stent, the crown having a series of connected or separated guide grooves for the circular stent to fill in the grooves when the prosthetic valve is transformed from the first helical pre-implantation configuration to the second valvular configuration.

One object of the invention provides a prosthetic valve system, wherein the crown is loaded with at least one bioactive agent selected from the group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, anti-infectives, and combination thereof. In a further embodiment, the crown is loaded with at least one bioactive agent selected from the group consisting of actinomycin D, paclitaxel, vincristin, methotrexate, angiopeptin, batimastat, halofuginone, sirolimus, tacrolimus, everolimus, tranilast, dexamethasone, mycophenolic acid, and stem cells.

One object of the invention provides a prosthetic valve system, wherein the prosthetic valve comprises a support structure with a circular stent and at least a hook secured at the support structure sized and configured for piercing into surrounding tissue. In one embodiment, at least a portion of the support structure is covered with cloth.

Some aspects of the invention relate to a method for implanting a prosthetic valve in a patient or an animal, comprising: providing a prosthetic valve system comprising a prosthetic valve having a first collapsed helical pre-implantation configuration that is reversibly transformable to a second valvular configuration, a radially (and/or helically) collapsible and expandable crown, the crown including a cylindrical support means for enclosing the prosthetic valve, and an elongate delivery apparatus; mounting the prosthetic valve at the first pre-implantation configuration and the crown at a collapsed configuration onto the delivery apparatus; delivering the delivery apparatus to a target implant site in the patient; expanding the crown at the implant site; deploying the prosthetic valve at the implant site by transforming the prosthetic valve from the first pre-implantation configuration to the second valvular configuration; and removing the delivery apparatus from the patient.

One object of the invention provides a method for implanting a prosthetic valve in a patient, wherein the implant site at a body organ or system is selected from the group consisting of a cardiovascular system, a venous system, an esophagus, a stomach, a ureter, a urethral, a biliary passage, and an intestine. In one embodiment, the delivery step of the method is selected from the group consisting of a percutaneous procedure, a trans-apical catheterization, an endoscopic procedure, a laparoscopic procedure, and an open-chest procedure.

Some aspects of the invention relate to a method of delivering at least one bioactive agent to a body channel of a patient, comprising: (a) providing an implant device loaded with the at least one bioactive agent, wherein the implant device is at a first helical pre-implantation configuration and a second circular configuration, wherein the first configuration is reversibly transformable to the second configuration; (b) delivering the implant device to about the body channel at the first configuration; (c) deploying the implant device at the body channel by transforming the implant device to the second configuration; and (e) releasing the at least one bioactive agent. In one embodiment, the implant device at the first configuration is helically wrapped around an elongate delivery apparatus for delivering to about the body channel of the patient. In another embodiment, the implant device comprises a carrier for loading the at least one bioactive agent, wherein the carrier is biodegradable or non-biodegradable.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

DETAILED DESCRIPTION OF THE EXEMPLARY EMBODIMENTS

The preferred embodiments of the present invention described below relate to an implantable prosthetic heart valve system in low profiles suitable for replacement of a defect or diseased human heart valve and methods of delivery. The preferred embodiments of the present invention described below relate particularly to a prosthetic valve in a pre-valve configuration that is reversably transformable to a functional open valve configuration. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

The term "pre-valve" is meant herein to indicate a valvular device at a pre-implantation stage when the device does not possess valvular functions. In general, the device of the present invention consists of two different configurations, which are reversably transformable from one to another. The device is in its initial substantially helically collapsed configuration for delivery through a delivery apparatus, such as a catheter, a wire, a guidewire, a flexible tubing, a cannula, or any elongate apparatus with minimal profiles for delivery. The procedure for delivering the device in its initial collapsed configuration (a pre-valve configuration) includes a percutaneous manner, an endoscopic manner, a laparoscopic manner, a trans-apical manner, and the like. The device can also be delivered and deployed in an open-chest operation, optionally combined with other surgical procedures. The device transforms to a functional valvular configuration when the device is deployed inside the heart, a blood vessel, a lymphatic vessel, or other body channel. In an alternate embodiment, the device may be removable from the implant site by transforming the device from the second open configuration to the first collapsed non-functional configuration for retrieval.

Figure 1:
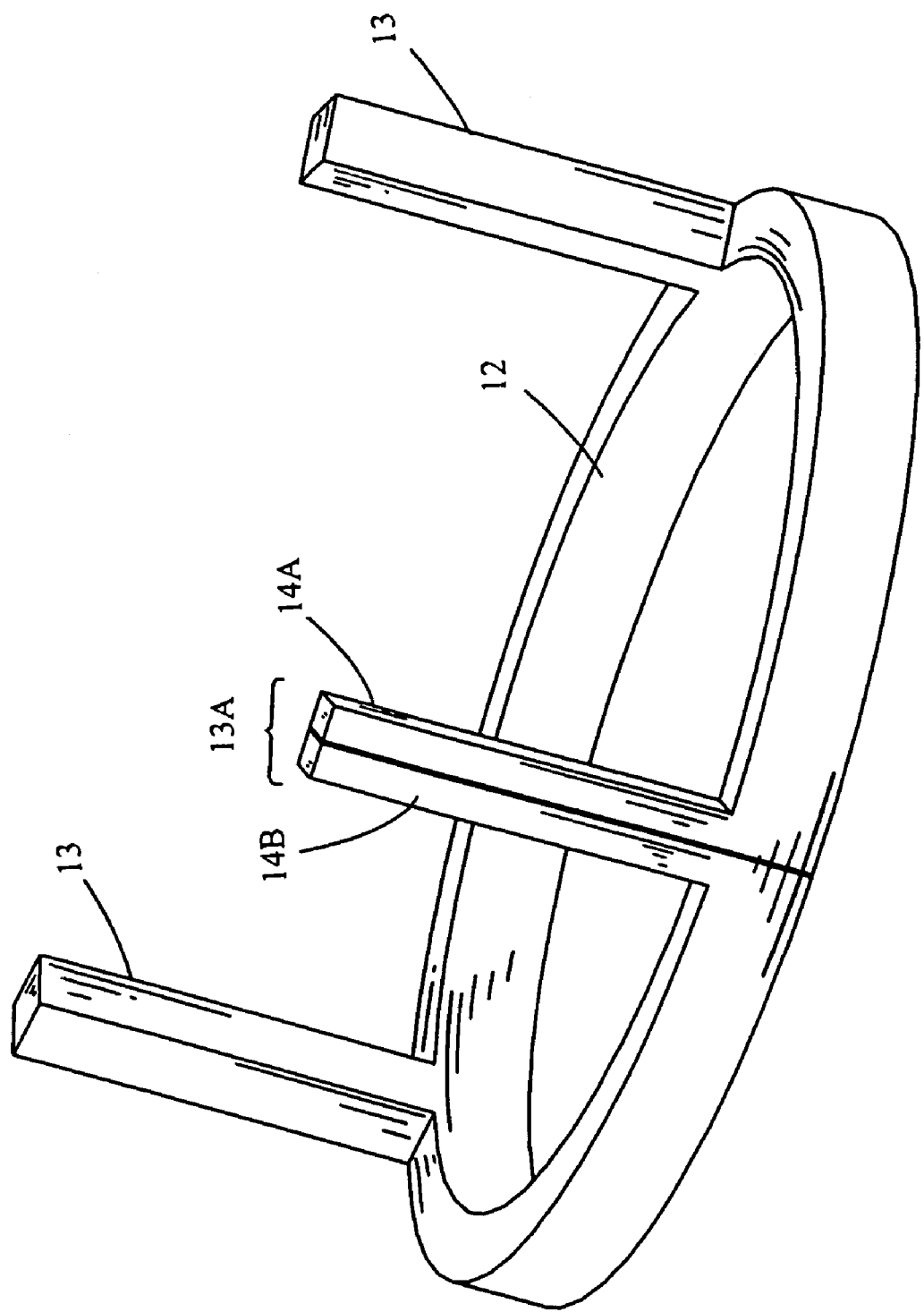
FIG. 1 shows a prosthetic valve in an open circular configuration (leaflets are not shown for simple illustration).
Figure 2:
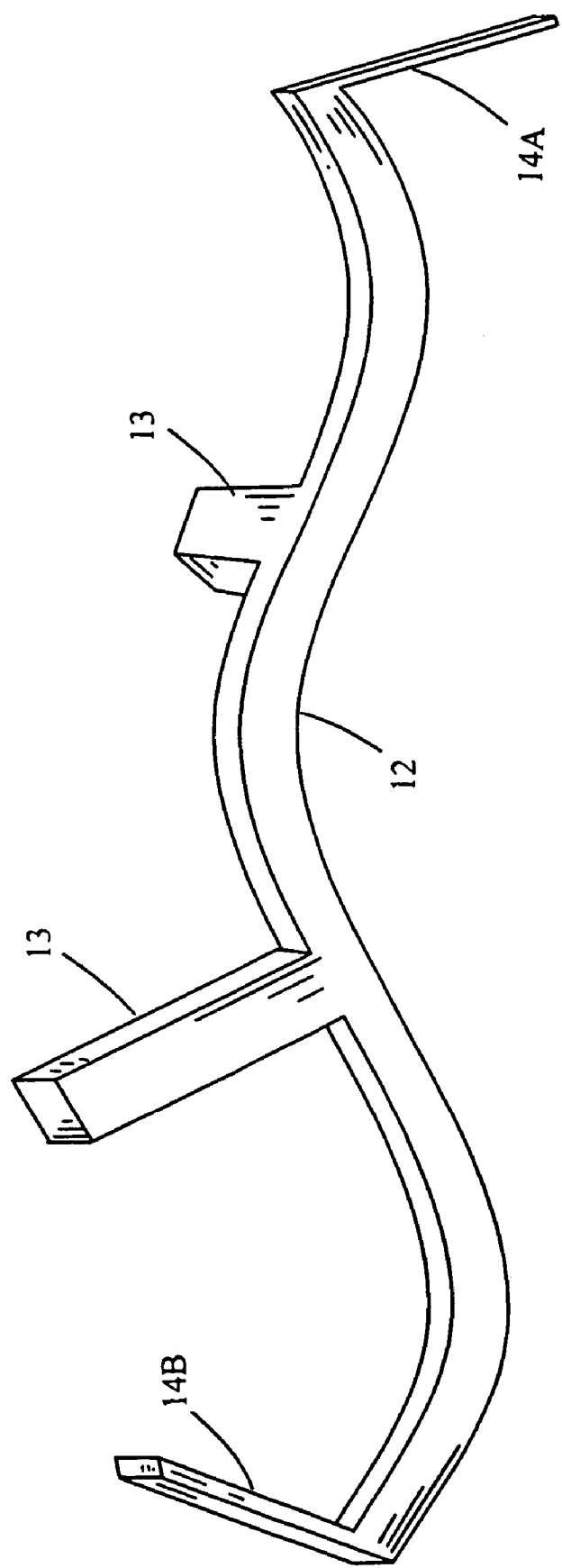
FIG. 2 shows a prosthetic valve of FIG. 1 in a non-circular configuration (leaflets are not shown for simple illustration).

FIG. 1 shows a prosthetic valve or flow-regulator in an open configuration whereas FIG. 2 shows the prosthetic valve in a non-circular non-linear collapsed configuration (leaflets are not shown for illustration purposes). The open configuration comprises a circular or any circular-like stent 12 with a number of support arms 13, 13A spaced apart that may be foldable by a specific angle from each other on the circular stent. In one example, three support arms are arranged about 120 degrees spaced apart from each other. Each support arm may have its own size, height, shape, or construction material according to the need of the prosthetic valve or implantation sites. The open configuration of FIG. 1 is used as the backbone of a flexible assembly for mounting compliant leaflets. The leaflet material may be made of synthetic material, engineered biological tissue, biological valvular leaflet tissue, pericardial tissue, or crosslinked pericardial tissue. In one embodiment, the pericardial tissue may be procured from bovine, equine, porcine, ovine, human, or other animals. In another embodiment, the crosslinked pericardial tissue is crosslinked with a crosslinking agent selected from the group consisting of formaldehyde, glutaraldehyde, dialdehyde starch, glyceraldehydes, cyanamide, diimides, diisocyanates, dimethyl adipimidate, carbodiimide, epoxy compound, and mixture thereof.

Figure 3:
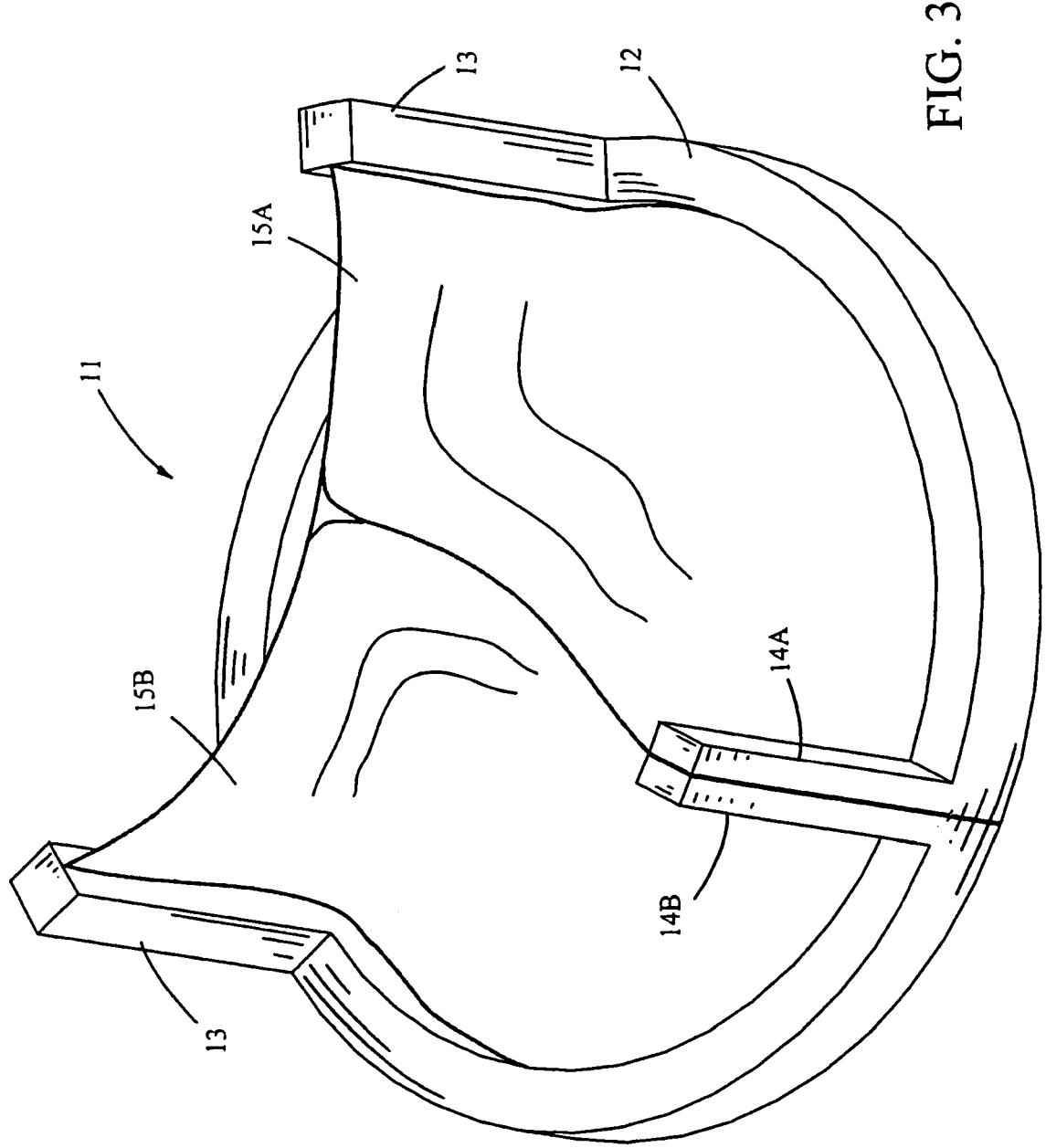
FIG. 3 shows a prosthetic valve in a functional valvular configuration with leaflets mounted.
Figure 4:
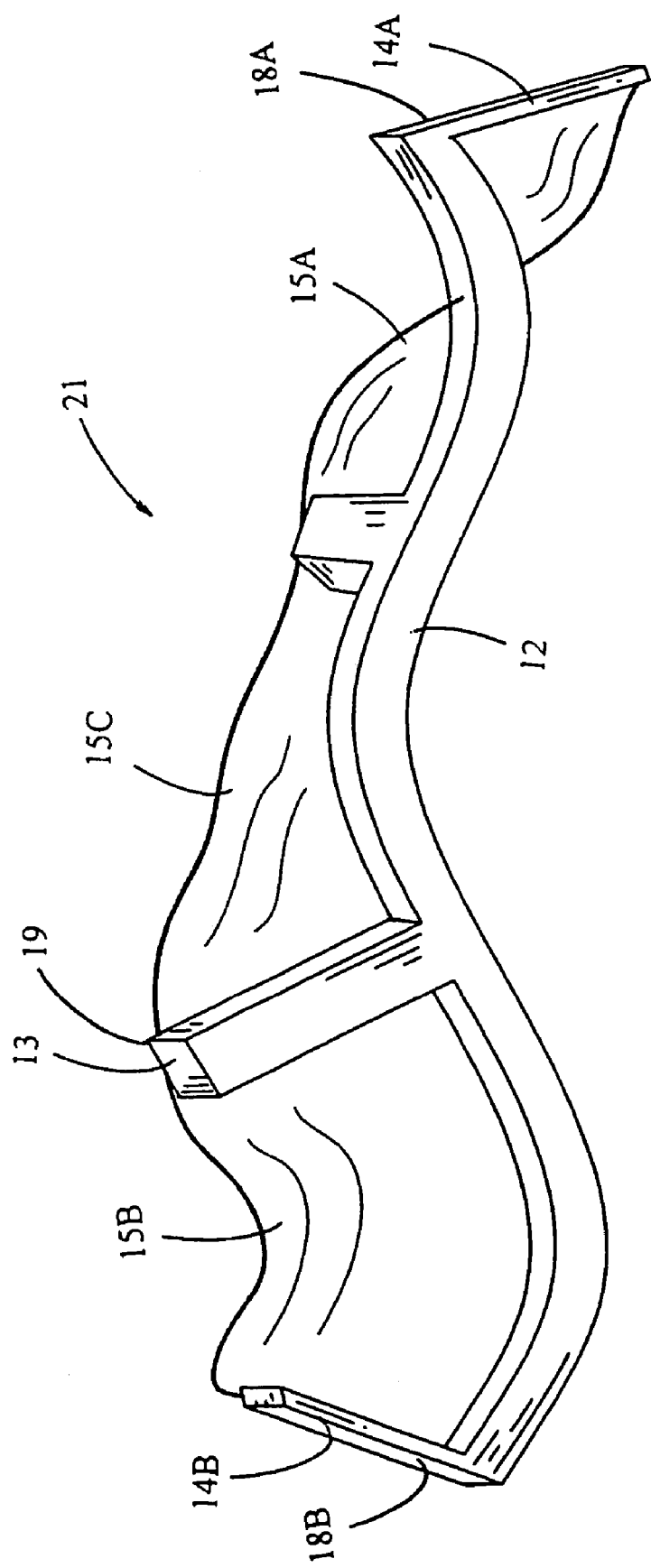
FIG. 4 shows a prosthetic valve of FIG. 3 in a non-functional, non-circular configuration with leaflets mounted.

FIG. 3 shows a prosthetic valve in a functional valvular configuration whereas FIG. 4 shows the prosthetic valve of FIG. 3 in a non-circular, non-functional configuration with leaflets 15A, 15B, 15C mounted (a pre-valve configuration). As illustrated, one support arm 13A comprises two matching beams 14A, 14B that are separable all the way through the stent 12 (that is, the stent is split at about the base of the split matching beams). By separating the matching beams, the valve of the present invention is transformable from a valvular configuration (as shown in FIG. 3) to a non-circular configuration (as shown in FIG. 4). In one embodiment, any functional valve similar to the one shown in FIG. 3 can be split along one support arm 13A to form a non-circular construct (similar to the one shown in FIG. 4) with a first leaflet 15A attached to a first beam 14A at one end of the construct and a second leaflet 15B attached to a second beam 14B at an opposite end of the construct. The leaflets are not altered or cut during the step of splitting the support arm 13A into two matching beams 14A and 14B. In a preferred embodiment, the non-circular configuration may be formed in a helical configuration collapsed around a delivery apparatus (for examples, a catheter, a cannula, a guidewire, or any tubular flexible apparatus). The delivery apparatus is generally in an elongate tubular shape. In one embodiment, the delivery apparatus may comprise a helical groove along its elongate body sized and configured to appropriately receive the helical-shaped collapsed pre-valve of FIG. 4.

In one embodiment, the beam 14A is sized and configured to match the beam 14B appropriately to form a support arm 13A in a beam-matching process. After deployment at the implant site, the formed support arm 13A has the required rigidity, stability, biocompatibility, and substantially seamless characteristics (such as leak-proof property) to support the leaflets and enables the open valve being functional. The first far-end surface 18A of the support beam 14A matches the second far-end surface 18B of the support beam 14B when the valve is in the valvular configuration as shown in FIG. 3. In one embodiment, at least a portion of the support beam 14A and the support beam 14B comprise opposite magnetic properties enabling the beam-matching with a magnet coupling force. In operations, the helically collapsed pre-valve with its support beams are placed inside a delivery sheath. Once the pre-valve is delivered at about the implant site, the sheath constraint is removed and the magnetic coupling forces enable beam-matching to transform the pre-valve to a functional valve. The beam-matching may comprise other types of coupling. For example, the first far-end surface 18A may comprise a plurality of protrusions whereas the second far-end surface 18B comprises the same number of matching recesses corresponding to those protrusions on the first far-end surface. In an alternate embodiment, the first far-end surface may have guide grooves or bias toward the second far-end surface for beam-matching or coupling.

In an alternate embodiment, the beam-matching process may utilize a suture and cinch technique with suture joining the first and second beams to draw the first and second beams into closer proximity and a cinch member to secure the suture to maintain the first and second beams in the closely matched position.

In one embodiment, the prosthetic valve 11 (in its valvular configuration with mounted leaflets) transforms to a helical valve 21 (in its non-functional configuration with mounted leaflets) by deforming the split stent 12 along with its components to a helix having a size of about 2 to 30 French diameters, preferably about 3 to 12 French diameters, and most preferably about 3 to 6 French diameters. The support arms and the attached leaflets might also be folded in the helical configuration. In one embodiment, the circular stent and/or the support arms of the valve are made of thermal shape memory material, such as Nitinol (a nickel-titanium alloy),-other biocompatible shape memory metals, or shape memory polymers. The use of shape memory material enables precise transformation of the non-circular collapsed valve 21 to the functional prosthetic valve 11 during implantation. The thermal shape memory Nitinol, its shape transformation characteristics, and medical device uses are documented in prior art and well known to one ordinary skilled in the art, for examples, U.S. Pat. No. 6,077,298 to Tu et al. and U.S. Pat. No. 6,890,350 to Walak.

One object of the invention provides a prosthetic valve that comprises a support structure with a circular or circular-like stent (without the support arms 13, 13A as shown in FIG. 1), wherein the stent is splittable into a non-circular stent with two ends, wherein the two ends are configured to be coupled to each other by a magnetic force or by a suture and cinch technique at the second valvular post-implantation configuration. In a further embodiment, at least a portion of the support structure is covered with cloths.

The helical configuration of the prosthetic pre-valve can be meticulously wrapped around the delivery apparatus, delivered through a body space and deployed at an atrio-ventricular, pulmonary, or aortic position in the heart, a venous, a lymphatic, a blood vessel, esophageal, urethral, and the like depending on the valve type and the need. One major advantage of the present invention is the low overall profile of the helical collapsed configuration that can be achieved by applying the helical concept in folding a material. In one embodiment, the profile of the collapsed configuration can be as small as the diameter of the delivery apparatus when the collapsed device is constrained and positioned in a groove (grooves) on the surface of the delivery apparatus. In another embodiment, the profile of the collapsed configuration can be as small as the diameter of the delivery apparatus plus the applicable thickness of the support arms or the device. As is well known to one ordinary skilled in the art, a conventional percutaneous valve system that is reversably collapsed radially during a delivery phase could only be loaded on a delivery apparatus of about 24 French diameters or larger. Furthermore, a conventional percutaneous valve might compressively impinge a portion of the leaflets of the tissue valve when the stent-structure is expanded by an inflatable balloon.

Some aspects of the invention provide an implant device loaded with the at least one bioactive agent, wherein the implant device is at a first helical pre-implantation configuration and a second circular configuration, wherein the first configuration is reversibly transformable to the second configuration. In one embodiment, the implant device comprises a carrier for loading the at least one bioactive agent, wherein the carrier is biodegradable or non-biodegradable. Some aspects of the invention provide a method of delivering at least one bioactive agent to a body channel of a patient, comprising: (a) providing an implant device loaded with the at least one bioactive agent, wherein the implant device is at a first helical pre-implantation configuration and a second circular configuration, wherein the first configuration is reversibly transformable to the second configuration; (b) delivering the implant device to about the body channel at the first configuration; (c) deploying the implant device at the body channel by transforming the implant device to the second configuration; and (e) releasing the at least one bioactive agent. In one embodiment, the implant device at the first configuration is helically wrapped around an elongate delivery apparatus for delivering to about the body channel of the patient.

Figure 5:
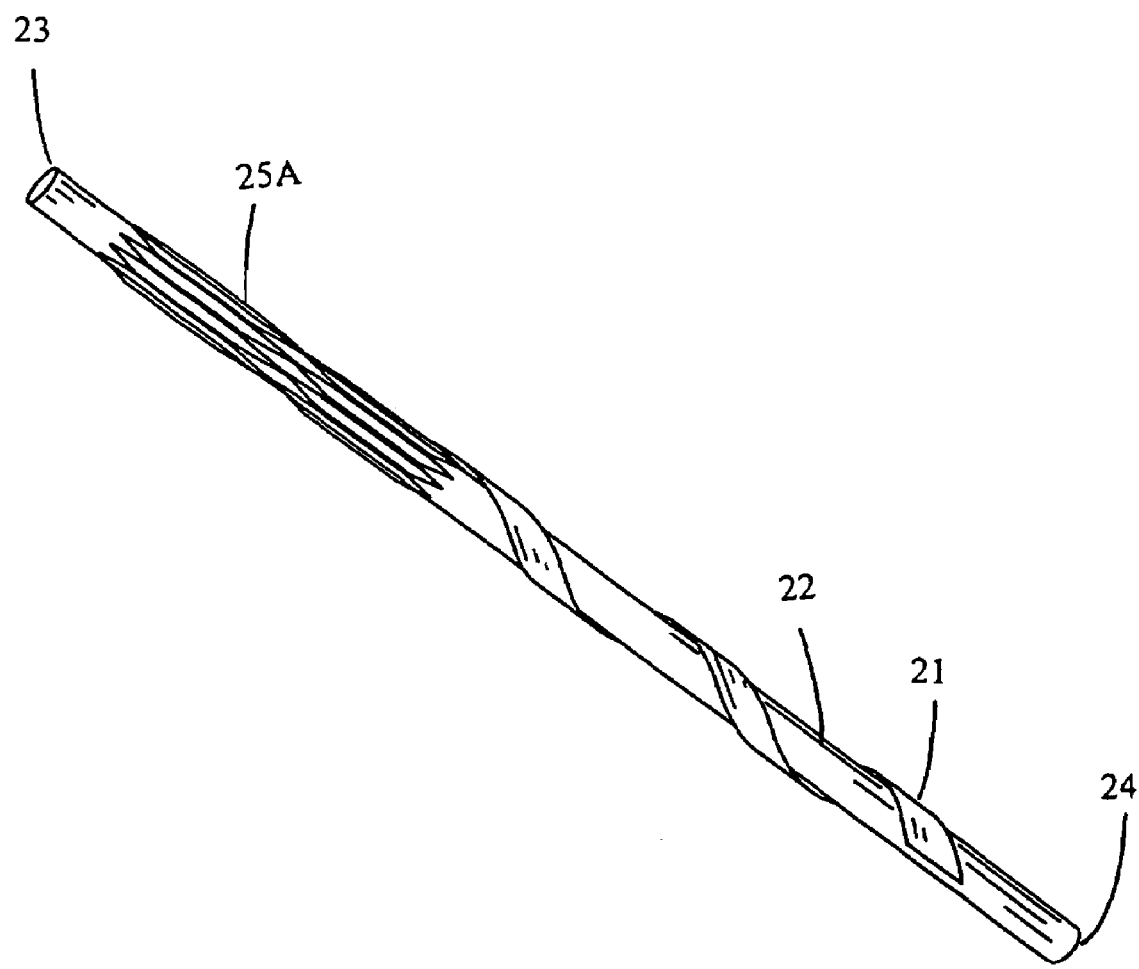
FIG. 5 shows a delivery apparatus with a helically collapsed valve and a collapsed crown configured for delivery to an implant site.

FIG. 5 shows a delivery apparatus 22 with a helical collapsed valve 21 and a collapsed crown 25A configured for delivery to an implant site. In one embodiment, the delivery system of the present invention comprises a delivery apparatus with a collapsed valve mounted thereon. In another embodiment, the present invention is intended to provide an attached or unattached element in the form of a crown to facilitate accurate positioning and stability of the prosthetic valve. In a preferred embodiment, the delivery apparatus comprises a distal end 23, a proximal end 24 and an elongate body between the distal and the proximal ends. The collapsed valve and/or the collapsed crown are securely mounted on the elongate body of the delivery apparatus during the delivery phase and are releasable during the deployment phase at the implant site. As further described below, the valve device of the invention can be delivered and implanted by a percutaneous, a trans-apical catheterization, an endoscopic, a laparoscopic, an open-chest, or other procedures.

For the mounted device of a crown unattached to the prosthetic valve, the implantation of the small prosthetic valve of the invention includes two stages. First, the crown in its helical collapsed configuration is delivered to a target implantation area and is expanded to position the crown in place. Second, the prosthetic valve is delivered, deployed, and positioned at about the entrance region of the crown platform. In one embodiment, the assembly of the valve and the crown at the deployed stage is provided by a series of connected or separated guide grooves (not shown) on the crown for the stent 12 to fill in the grooves when the valve is transformed from its helical collapsed configuration to a functional valvular configuration.

For the mounted device of a crown attached to the prosthetic valve on the delivery apparatus, the crown segment and the valve segment are delivered to a target area together. The crown is fastened to the surrounding tissue by expanding the collapsed crown to a desired diameter. Thereafter, the valve transforms to a valvular open configuration following the deployment of the crown segment at the target implant site. In one embodiment, a suture joining a first portion of the expanded crown and a first portion of the deployed open valve is utilized to draw the two first portions into closer proximity and a cinch member to secure the suture to maintain the first portion of the crown and the corresponding first portion of the valve in a closely matched position (i.e., a suture and cinch technique). Repeatedly, the same suturing technique can be performed to closely join a second portion of the expanded crown and a corresponding second portion of the deployed open valve.

A crown, crown-guide, or crown element to form a support for the implantable valve is shown in a collapsed configuration (as 25A in FIG. 5) during the delivery phase and in an expanded configuration (as 25B in FIG. 6) at the implantation phase. The crown may be placed in any valvular position and is intended to provide several functions as:

to inflate the valvular annulus;

to resist the recoil force from the annulus, thus preventing wall collapse;

to prevent the implantable valve from collapsing due to the recoil force at the annulus position;

to hold the valve in place;

to mitigate the process of tissue overgrowth with loading of drug/gene or at least one bioactive agent on the crown; and to provide a fastening/anchoring system for securing the open valve in place.

In an alternate embodiment, the crown has barbed means to anchor the crown to the wall of the target implant site.

The crown may be loaded with at least one bioactive agent selected from the group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, anti-infectives, and combination thereof. In a further embodiment, the crown may be loaded with at least one bioactive agent selected from the group consisting of actinomycin D, paclitaxel, vincristin, methotrexate, angiopeptin, batimastat, halofuginone, sirolimus, tacrolimus, everolimus, tranilast, dexamethasone, mycophenolic acid, and stem cells.

The crown may be expanded by an inflatable balloon that is positioned beneath the collapsed crown 25A. The inflatable balloon is in fluid communication to inflatable fluid outside of the body through a lumen of the delivery apparatus. In an alternate embodiment, the crown may be expanded using a shape memory material (metallic or nonmetallic). The shape recovery (or shape transition) temperature of a shape memory material (e.g., Nitinol) is distinct from the living body temperature, for example, a shape recovery temperature at about 38 to 55° C., preferably between about 40 and 45° C. In one embodiment, the temperature elevation could be provided by connecting the crown to an external radiofrequency source through an insulated wire, wherein the distal end of the wire is uninsulated and functions as an electrode that lies beneath and removably connected to the collapsed crown. Under a predetermined power level and power duration, the electrode delivers adequate radiofrequency energy to raise the crown temperature to above the shape recovery temperature of the construction material. In an alternate embodiment, a dose of hot saline may be injected to raise the crown temperature to above the shape recovery temperature of the construction material. The open configuration of the crown is generally a cylindrical wireform shape that can be transformed to its collapsed configuration by crimping or folding over a tubular body of the delivery apparatus.

In one embodiment, the tissue valve is constructed by sewing the individual leaflets obtained from an animal valve to a stent to hold the leaflets in proper position as a stented valve. The tissue valve applicable in the current invention may be constructed by configuring valve leaflets from the pericardial sac of cows or horses and sewing them to an annulus stent support as a pericardium valve. The annular stent support may be rigid or slightly flexible and covered with cloth (usually a synthetic material sold under the trademark Dacron® or Teflon®) for fixation to the patient's native tissue. In one aspect, the annulus stent support comprises a cloth cover, wherein the cloth cover is made of polystyrene, polyester, expanded polytetrafluoroethylene, or other biocompatible material. In one embodiment, the porcine, bovine, ovine or equine tissue is chemically treated to alleviate any antigenicity.

The main advantage of tissue valves is that they do not cause blood clots to form as readily as do the mechanical valves, and therefore, the tissue valves do not typically require life-long systemic anticoagulation. Another advantage is that a tissue valve is so flexible that it can be shaped and configured for delivery percutaneously or endoluminally. It is one aspect of the present invention to provide a prosthetic heart valve with the transformable configurations having flexibility of transforming from a helical configuration with minimal profiles at a delivery phase to functional valvular configuration. Therefore, it would be desirable to provide a delivery system for delivering a prosthetic heart valve to a patient's heart configured to be releasably folded on a delivery apparatus or inside a lumen of the delivery system through a percutaneous or percutaneous intercostal penetration of a patient's chest or an opening at a carotid artery, jugular vein, subclavian vein, femoral vein, femoral artery and other blood vessel.

EXAMPLE No. 1

Valve Deployment

Figure 6:
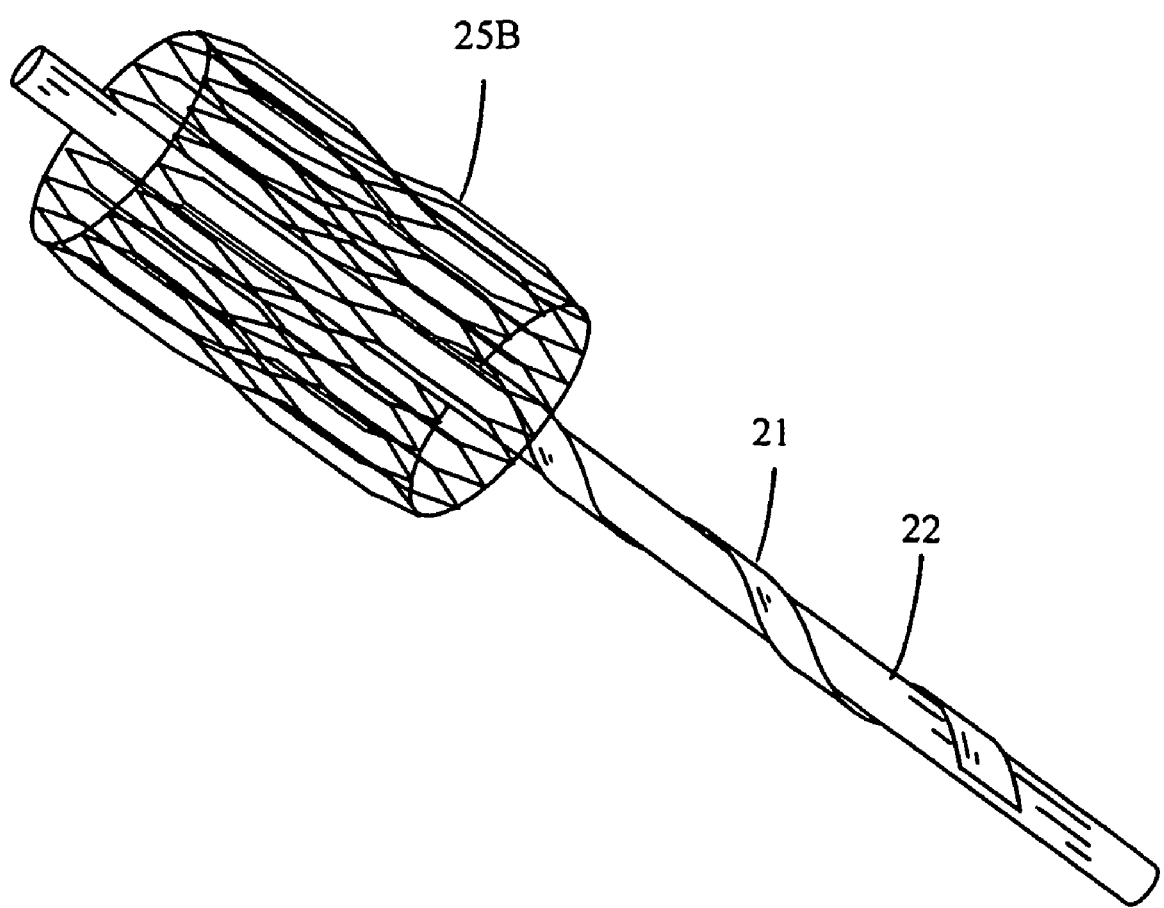
FIG. 6 shows a delivery apparatus with a helically collapsed valve and an expanded crown at an implant site.

FIGS. 5-8 show some general steps of implanting a prosthetic valve in a patient. In operations, a delivery apparatus 22 with a non-circular collapsed valve (i.e., a pre-valve) 21 in a helical manner and a collapsed crown 25A are configured for delivery to an implant site of the patient. In one embodiment, the distal end 23 of the delivery apparatus pierces into a patient's vasculature or cardiac apex. By way of illustration, the crown that is radially and/or helically contracted and releasably mounted onto a balloon portion of the delivery apparatus is guided and forwarded to a target body site. As shown in FIG. 6, the crown is expanded to its intended open configuration 25B either through shape recovery mechanism or balloon expansion. The crown, thereafter, maintains its expanded shape even at the living body temperature.

Figure 7:
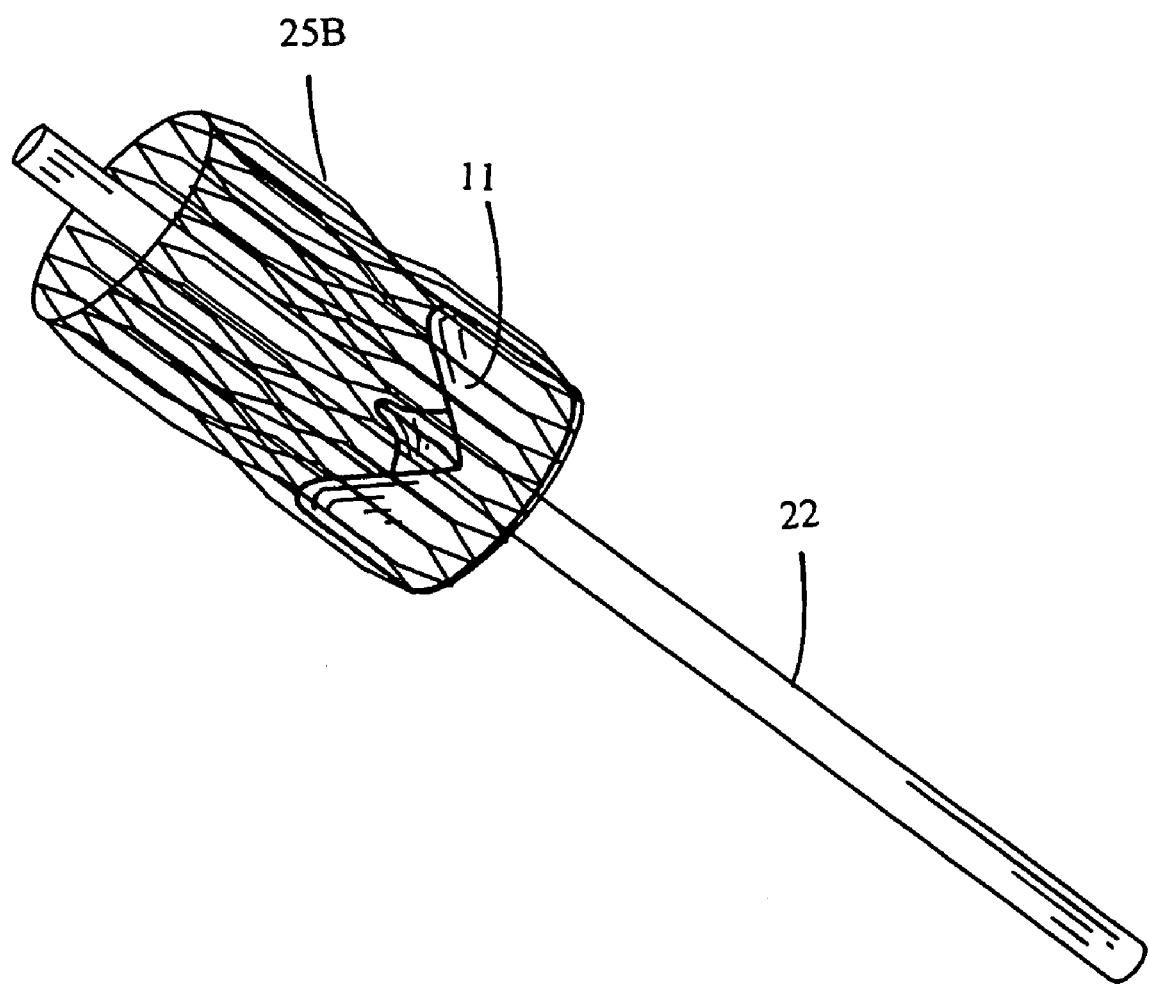
FIG. 7 shows a delivery apparatus with an expanded, deployed valve and an expanded crown at an implant site.
Figure 8:
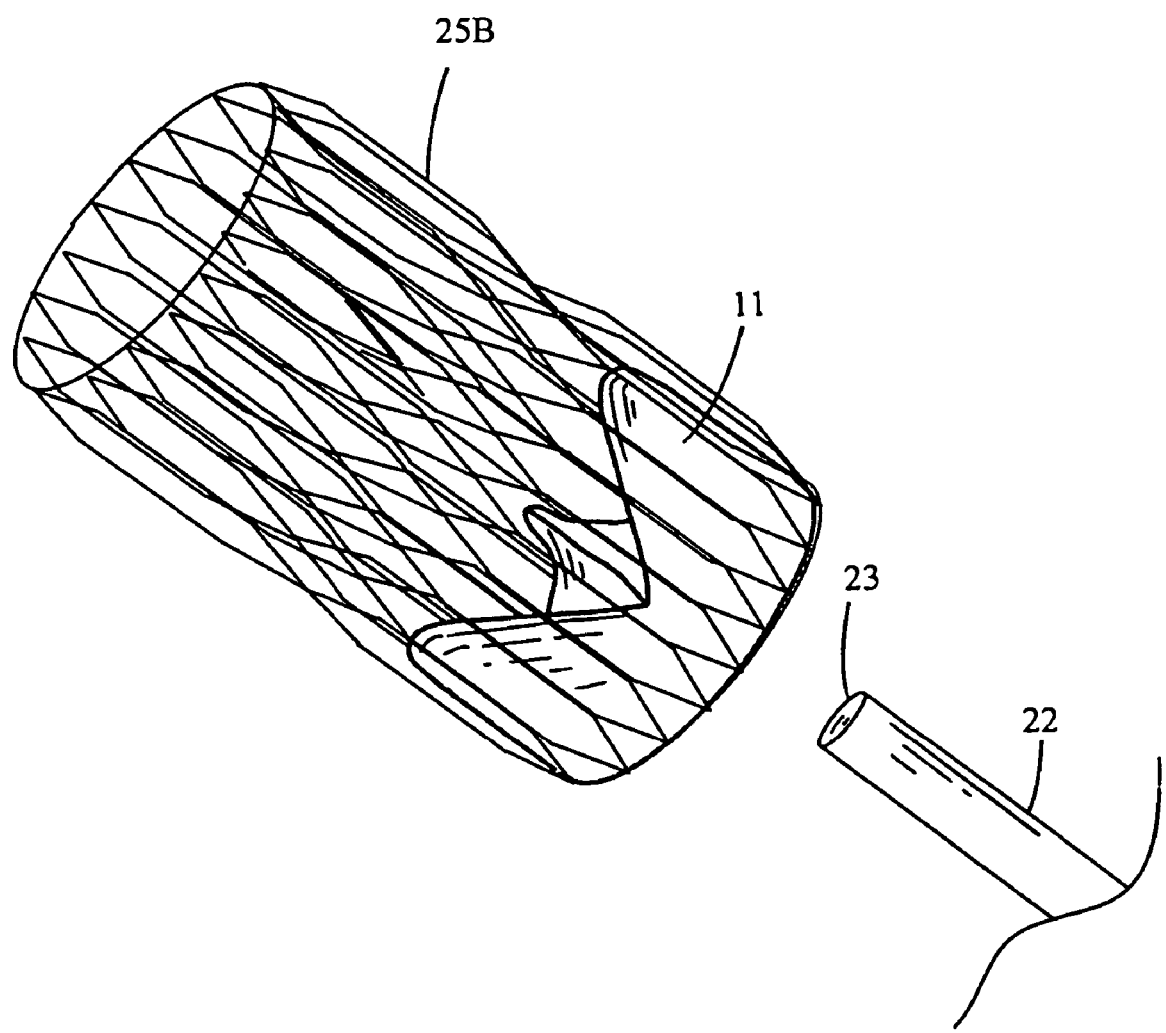
FIG. 8 shows an expanded, deployed valve and an expanded crown at an implant site while the delivery apparatus is pulled out of the annulus of the device.

FIG. 7 shows a delivery apparatus with an expanded, deployed valve 11 and an expanded crown 25B at an implant site whereas FIG. 8 shows a last step of operations when the delivery apparatus 22 is pulled out of the annulus site of the patient.

Figure 9:
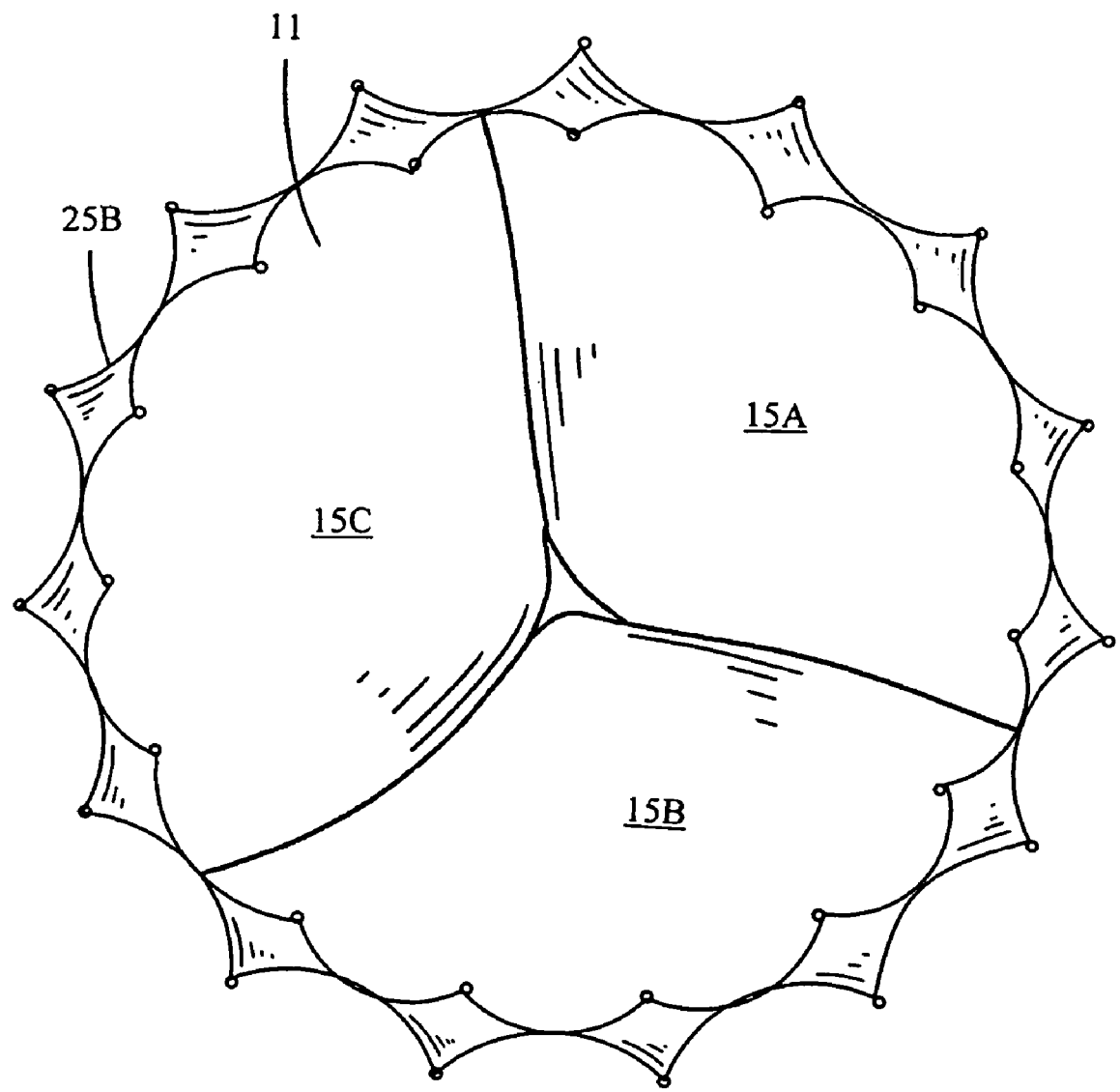
FIG. 9 shows a top-view of an expanded functional valve inserted inside the crown.
Figure 10:
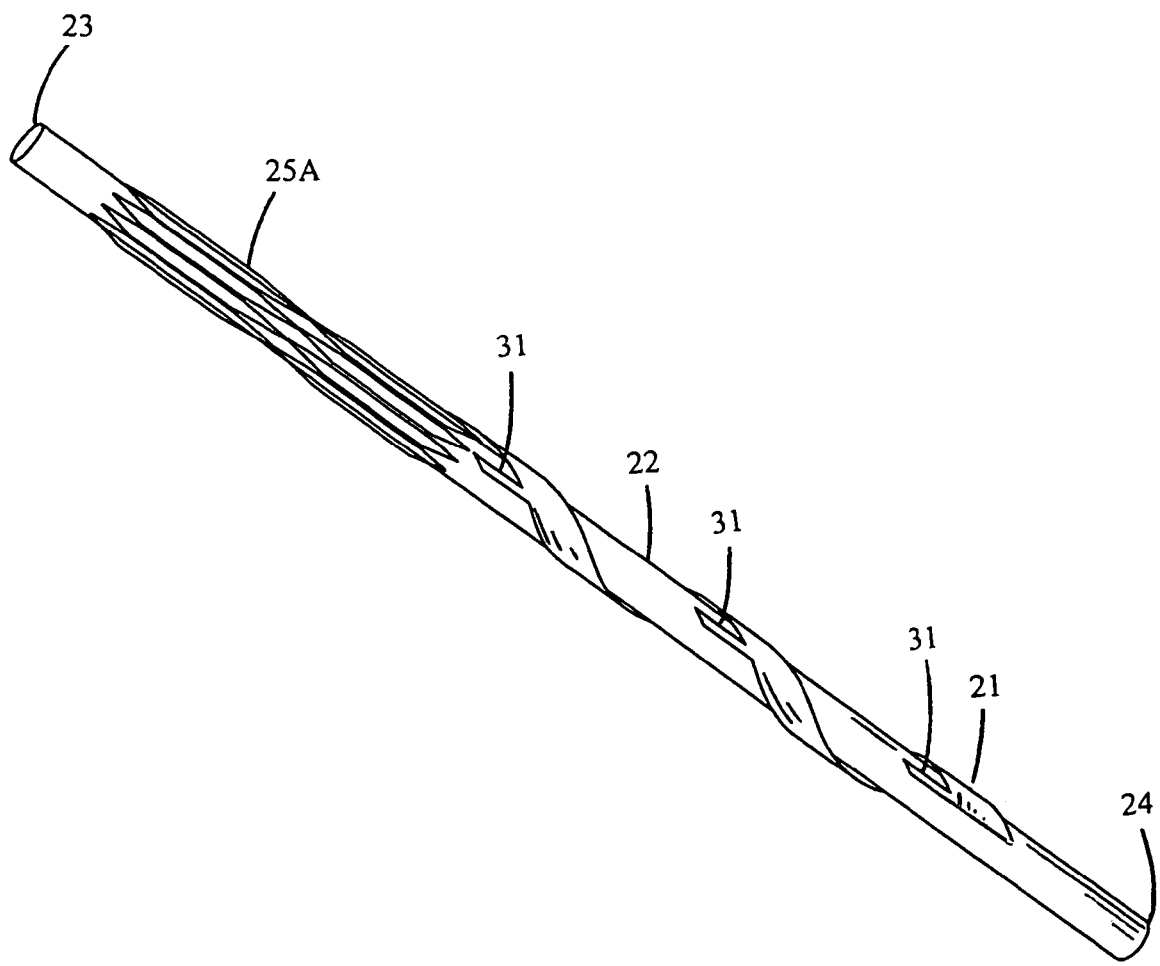
FIG. 10 shows a delivery apparatus with a helically collapsed valve having a hook and a collapsed crown configured for delivery to an implant site.
Figure 11:
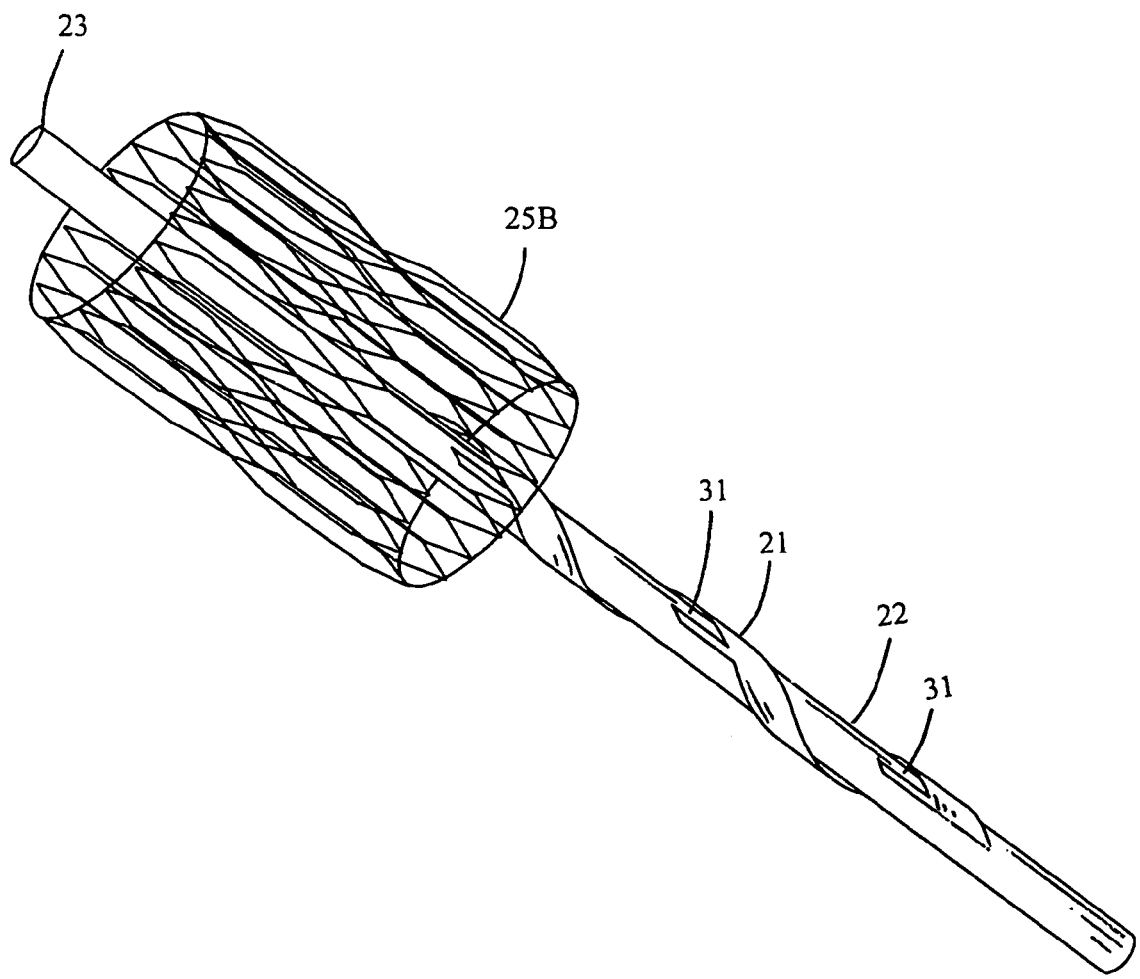
FIG. 11 shows a delivery apparatus with a helically collapsed valve having a hook and an expanded crown at an implant site.
Figure 12:
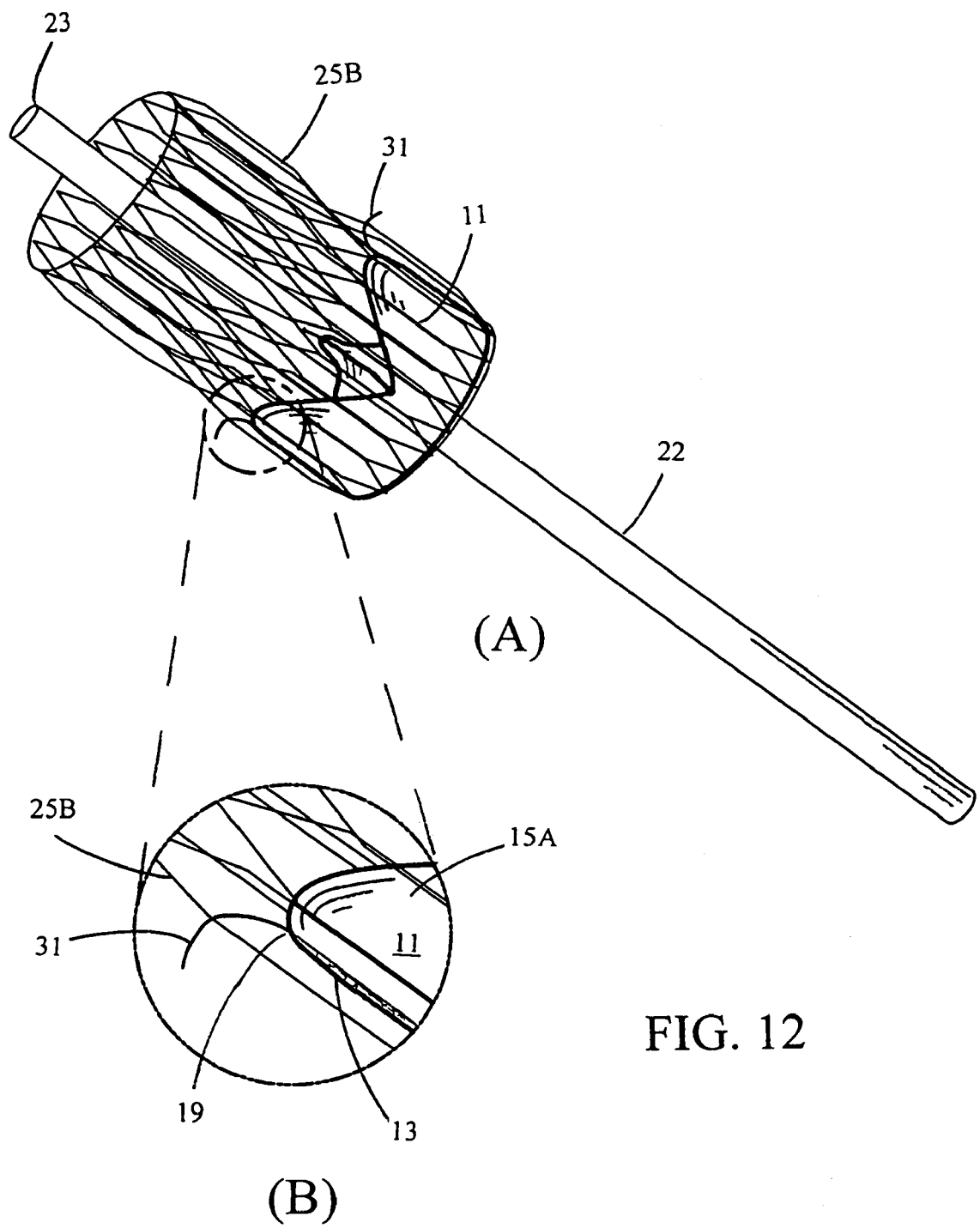
FIG. 12(A) shows a delivery apparatus with an expanded, deployed valve having a hook and an expanded crown at an implant site.
FIG. 12(B) shows an enlarged illustration of the expanded, deployed valve having a hook of FIG. 12(A).

FIG. 9 shows a top-view of an expanded valve 11 inserted inside the crown 25B. The edge of the expanded crown against the inner wall of the tissue at the implantation site is generally sealed due to the outward force to counter the recoil force of the annulus. Other means for sealing the edge space may be applicable, for example, covering at least a portion of the exterior surface of the crown with cloths so to provide "filling" to the edge space. In an alternate embodiment, the edge space is filled with a sealant, such as fibrin glue, synthetic glue, and the like.

Figure 13:
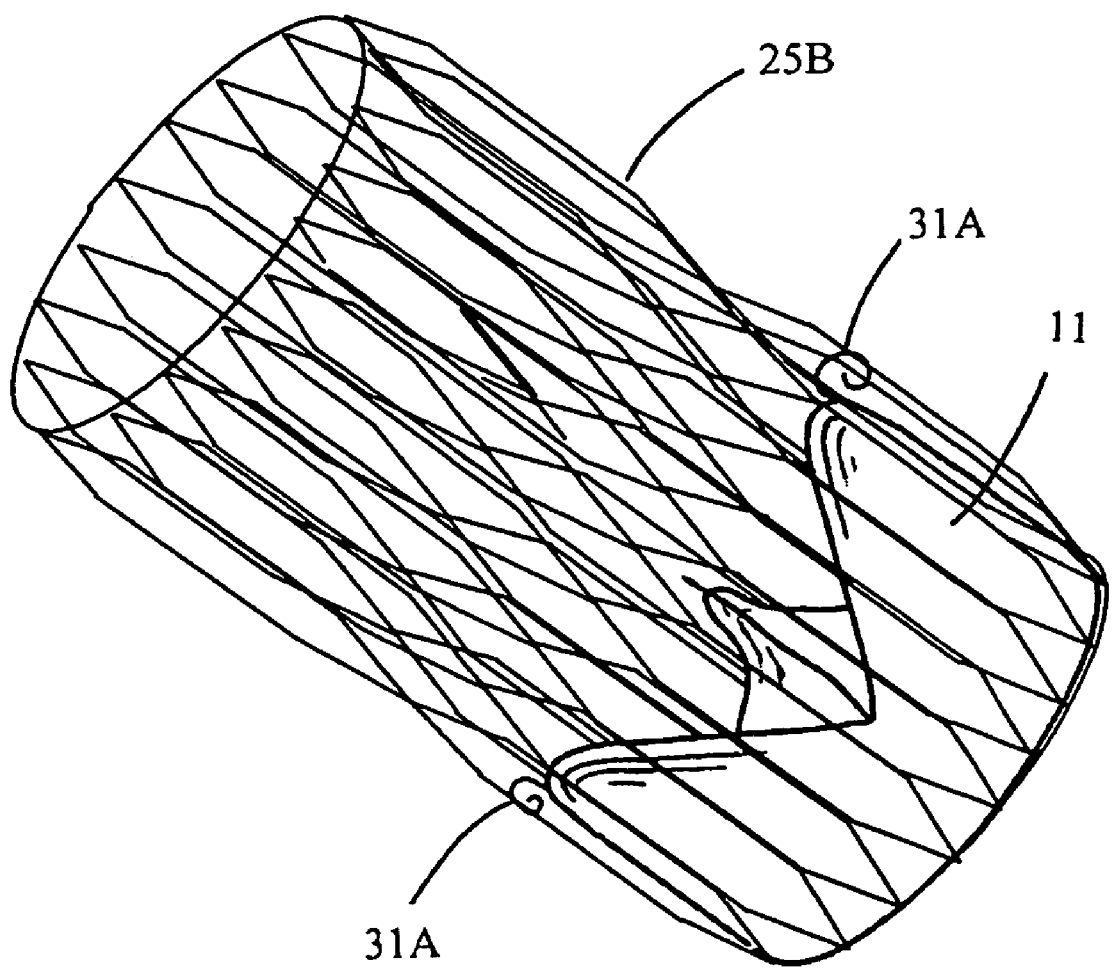
FIG. 13 shows an embodiment of the expanded, deployed valve having a clasp-like mechanism inside the expanded crown.

Some aspects of the invention provide a mechanism for positioning and/or securing the valve to its crown. FIG. 10 to FIG. 12(A) and 12(B) show an alternate embodiment of a delivery apparatus 22 with a helically collapsed valve 21 having at least a hook 31 and a collapsed crown 25A and their delivered configuration at an implant site. In one embodiment, the hook 31 lies along the same plane of the helically collapsed valve in a first configuration (called as "appendix") so as to minimize the profile during the delivery phase. The appendix transforms to a second configuration (called "shook") when the valve is placed at any designated position. The appendix or hook may be made of shape memory material (for example, Nitinol) attached at the conjunction of the leaflet cusps. The appendices have superelastic properties or thermal shape memory properties at body temperature and turn to a hook shape when they are exposed to body temperature or at some elevated shape transition temperature discussed above. In one embodiment, the hook would be locked in the crown structure to provide clasp-like mechanism (FIG. 13) for securing the valve inside the crown. Thus, the valve would be secured within the crown when the appendices turn into their hook-like configuration. In one embodiment, the hook can take other configurations, such as needle-like projection or prongs that may bend to have a radial orientation. In a further embodiment, the prosthetic valve comprises at least a hook 31 or hook-like anchoring mechanism at a distal end 19 of the support arms 13 adapted for stabilizing the valve at the implant site.

In one embodiment, the valve system of the invention with low profiles during a delivery phase may be used to replace or substitute a valve in the cardiovascular system, in a venous system, in the esophagus, at the stomach, in the ureter and/or vesica, in the biliary passages, or in the intestine. In operations, the prosthetic valve of the invention could be used in antegrade or retrograde transcatheter implantation of a valve, such as an aortic valve. In one embodiment, the crown or crown-guide may be sized 5 to 25% larger than the diameter of the annulus of the implant site.

Therefore, some aspect of the present invention is to provide a method for implanting a prosthetic valve in a patient, comprising:

(a) providing a prosthetic valve system comprising a prosthetic valve having a first helical pre-implantation configuration that is reversibly transformable to a second valvular configuration, a radially or helically collapsible and expandable crown, the crown including a cylindrical support means for enclosing the prosthetic valve, and an elongate delivery apparatus;

(b) mounting the prosthetic valve at the first pre-implantation configuration and the crown at a collapsed configuration onto the delivery apparatus;

(c) delivering the delivery apparatus to a target implant site in the patient;

(d) expanding the crown at the implant site;

(e) deploying the prosthetic valve at the implant site by transforming the prosthetic valve from the first pre-implantation configuration to the second valvular configuration; and (f) removing the delivery apparatus from the patient.

Although the present invention has been described with reference to specific details of certain embodiments thereof, it is not intended that such details should be regarded as limitations upon the scope of the invention. Many modifications and variations are possible in light of the above disclosure.

What is claimed is:

1. A prosthetic valve for implantation in a patient comprising a first helical pre-implantation configuration and a second functional valvular configuration, wherein said first configuration is reversibly transformable to said second configuration, wherein said valve comprises: a support structure with leaflets mounted thereon, said support structure comprising a circular stent and a plurality of elongate support arms, and wherein a first support arm is splittable into two support beams along a longitudinal axis of said first support arm, said two support beams being subsequently capable of being structurally re-attached to enable a reversible transformation of said second configuration into said first configuration.

2. The prosthetic valve of claim 1, wherein said valve comprises a support structure with leaflets mounted thereon, wherein the leaflets are made from material selected from a group consisting of synthetic material, engineered biological tissue, biological valvular leaflet tissue, pericardial tissue, and crosslinked pericardial tissue.

3. The prosthetic valve of claim 2, wherein the pericardial tissue is selected from a group consisting of bovine, equine, porcine, ovine, and human tissue.

4. The prosthetic valve of claim 2, wherein the crosslinked pericardial tissue is crosslinked with a crosslinking agent selected from a group consisting of formaldehyde, glutaraldehyde, dialdehyde starch, glyceraldehydes, cyanamide, diimides, diisocyanates, dimethyl adipimidate, carbodiimide, epoxy compounds, and mixture thereof.

5. The prosthetic valve of claim 2, wherein at least a portion of the support structure is covered with cloth.

6. The prosthetic valve of claim 5, wherein at least a portion of the leaflets is covered with cloth.

7. The prosthetic valve of claim 6, wherein at least one of said elongate support arms further comprises a hook at a distal end of said one elongate support arm.

8. The prosthetic valve of claim 6, wherein said stent is made of a shape memory material.

9. The prosthetic valve of claim 6, wherein said stent is made of shape memory Nitinol.

10. The prosthetic valve of claim 6, wherein the two support beams are coupled to each other by a magnetic force at the second valvular post-implantation configuration.

11. The prosthetic valve of claim 6, wherein a first of the two support beams is coupled to a second of the two support beams by a suture and cinch technique at the second valvular post-implantation configuration.

12. The prosthetic valve of claim 6, wherein at least a portion of the support structure is covered with cloth.

13. The prosthetic valve of claim 1, wherein said valve comprises a support structure with leaflets mounted thereon, said support structure comprising a circular stent, wherein said circular stent is splittable into a non-circular stent with two ends.

14. The prosthetic valve of claim 13, wherein at least one of said two ends further comprises a hook at a distal end of said at least one end.

15. A prosthetic valve system for implantation in a body channel comprising:

a prosthetic valve having a first helical pre-implantation configuration that is reversibly transformable to a second valvular configuration;

a prosthetic valve for implantation in a patient comprising a first helical pre-implantation configuration and a second functional valvular configuration, wherein said first configuration is reversibly transformable to said second configuration wherein said valve comprises: a support structure with leaflets mounted thereon, said support structure comprising a circular stent and a plurality of elongate support arms, and wherein a first support arm is splittable into two support beams along a longitudinal axis of said first support arm, said two support beams being subsequently capable of being structurally re-attached to enable a reversible transformation of said second configuration into said first configuration; and a radially or helically collapsible and expandable crown, the crown including a cylindrical support means for enclosing said prosthetic valve.

16. The prosthetic valve system of claim 15, wherein said crown is expandable by an inflatable balloon technique.

17. The prosthetic valve system of claim 15, wherein said crown in made of a shape memory material.

18. The prosthetic valve system of claim 15, wherein said crown in made of shape memory Nitinol.

19. The prosthetic valve system of claim 15, wherein said prosthetic valve is attached to the cylindrical support means of said crown.

20. The prosthetic valve system of claim 15, further comprising an elongate delivery apparatus, wherein said prosthetic valve at the first pre-implantation configuration and said crown are collapsibly mounted onto said delivery apparatus.

21. The prosthetic valve system of claim 20, wherein said prosthetic valve at the first pre-implantation configuration is removably mounted onto said delivery apparatus in a helical manner on the elongate delivery apparatus.

22. The prosthetic valve system of claim 21, wherein a profile of said mounted prosthetic valve is about 3 to 12 French diameter.

23. The prosthetic valve system of claim 21, wherein a profile of said mounted prosthetic valve is about 3 to 6 French diameter.

24. The prosthetic valve system of claim 21, wherein an exterior surface of said delivery apparatus comprises a helical groove sized and configured to receive the mounted prosthetic valve.

25. The prosthetic valve system of claim 21, wherein said delivery apparatus is selected from a group consisting of a catheter, a wire, a guidewire, a flexible tubing, and a cannula.

26. The prosthetic valve system of claim 15, wherein said prosthetic valve comprises a support structure with a circular stent, said crown having a series of connected or separated guide grooves for the circular stent to fill in the grooves when the prosthetic valve is transformed from the first helical pre-implantation configuration to the second valvular configuration.

27. The prosthetic valve system of claim 15, wherein said crown is loaded with at least one bioactive agent selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, anti-infectives, and combination thereof.

28. The prosthetic valve system of claim 15, wherein said crown is loaded with at least one bioactive agent selected from a group consisting of actinomycin D, paclitaxel, vincristin, methotrexate, angiopeptin, batimastat, halofuginone, sirolimus, tacrolimus, everolimus, tranilast, dexamethasone, mycophenolic acid, and stem cells.

29. The prosthetic valve system of claim 15, wherein said prosthetic valve comprises a support structure with a circular stent and at least a hook secured at said support structure sized and configured for piercing into surrounding tissue.

30. The prosthetic valve system of claim 29, wherein at least a portion of the support structure is covered with cloth.

31. A method for implanting a prosthetic valve in a patient, comprising: a prosthetic valve for implantation in a patient comprising a first helical pre-implantation configuration and a second functional valvular configuration, wherein said first configuration is reversibly transformable to said second configuration, wherein said valve comprises: a support structure with leaflets mounted thereon, said support structure comprising a circular stent and a plurality of elongate support arms, and wherein a first support arm is splittable into two support beams along a longitudinal axis of said first support arm, said two support beams being subsequently capable of being structurally re-attached to enable a reversible transformation of said second configuration into said first configuration, and a radially or helically collapsible and expandable crown, the crown including a cylindrical support means for enclosing said prosthetic valve, and an elongate delivery apparatus; mounting said prosthetic valve at the first pre-implantation configuration and said crown at a collapsed configuration onto said delivery apparatus; delivering said delivery apparatus to a target implant site in the patient; expanding said crown at the implant site; deploying said prosthetic valve at the implant site by transforming said prosthetic valve from the first pre-implantation configuration to the second valvular configuration; and removing the delivery apparatus from the patient.

32. The method of claim 31, wherein the implant site at a body organ or system is selected from a group consisting of a cardiovascular system, a venous system, an esophagus, a stomach, a ureter, a urethral, a biliary passage, and an intestine.

33. The method of claim 31, wherein the delivery step is selected from a group consisting of a percutaneous procedure, a trans-apical catheterization, an endoscopic procedure, a laparoscopic procedure, and an open-chest procedure.

34. A method of delivering at least one bioactive agent to a body channel of a patient, comprising: providing an implant device loaded with said at least one bioactive agent, wherein a prosthetic valve for implantation in a patient comprising a first helical pre-implantation configuration and a second functional valvular configuration, wherein said first configuration is reversibly transformable to said second configuration, wherein said valve comprises: a support structure with leaflets mounted thereon, said support structure comprising a circular stent and a plurality of elongate support arms, and wherein a first support arm is splittable into two support beams along a longitudinal axis of said first support arm, said two support beams being subsequently capable of being structurally re-attached to enable a reversible transformation of said second configuration into said first configuration; delivering said implant device to about said body channel at said first configuration; deploying said implant device at said body channel by transforming the implant device to said second configuration; and releasing said at least one bioactive agent.

35. The method of claim 34, wherein said implant device at said first configuration is helically wrapped around an elongate delivery apparatus for delivering to about said body channel of the patient.

36. The method of claim 34, wherein said implant device comprises a carrier for loading said at least one bioactive agent.

37. The method of claim 36, wherein said carrier is biodegradable.

* * * * *